United States Patent [19]

Humphries et al.

[11] Patent Number: 5,414,060
[45] Date of Patent: May 9, 1995

[54] ORAL HYGIENE COMPOSITIONS AND POLYMERS ACTIVE THEREIN

[75] Inventors: Martyn Humphries, Manchester; Jozef Nemcek; Joseph F. Jaworzyn, both of Cheshire; John B. Cantwell, Merseyside; John J. Gerrard, Cheshire, all of England

[73] Assignee: Imperial Chemical Industries PLC, London, England

[21] Appl. No.: 239,533

[22] Filed: May 9, 1994

Related U.S. Application Data

[60] Division of Ser. No. 761,463, Sep. 18, 1991, Pat. No. 5,336,728, which is a division of Ser. No. 496,150, Mar. 19, 1990, Pat. No. 5,079,288, which is a continuation of Ser. No. 16,257, Feb. 19, 1987, abandoned, which is a division of Ser. No. 793,763, Nov. 1, 1985, abandoned.

[30] Foreign Application Priority Data

Nov. 12, 1984 [GB] United Kingdom ........... 8428523

[51] Int. Cl.⁶ ............................................. C08F 8/14
[52] U.S. Cl. ................................. 524/558; 524/560
[58] Field of Search .............................. 524/558, 560

[56] References Cited

U.S. PATENT DOCUMENTS

| | | | |
|---|---|---|---|
| 4,200,563 | 4/1980 | Komiya | 526/287 |
| 4,230,844 | 10/1980 | Chang et al. | 526/210 |
| 4,270,953 | 6/1981 | Nakagawa et al. | 106/16 |
| 4,429,097 | 1/1984 | Chang et al. | 526/317 |
| 4,435,556 | 3/1984 | Masler, III | 526/317 |
| 4,476,252 | 10/1984 | Esselborn et al. | 521/172 |

FOREIGN PATENT DOCUMENTS

| | | |
|---|---|---|
| 0084782 | 8/1983 | European Pat. Off. |
| 852399 | 10/1958 | United Kingdom |
| 1144240 | 3/1969 | United Kingdom |
| 2005281 | 4/1979 | United Kingdom |
| 2148913 | 6/1985 | United Kingdom |
| WO8400371 | 2/1984 | WIPO |

Primary Examiner—Bernard Lipman
Attorney, Agent, or Firm—Cushman Darby & Cushman

[57] ABSTRACT

Oral hygiene compositions effective for preventing the adherent deposition of cariogenic bacteria on teeth comprise as active constituents polymers having defined repeating units comprising hydrocarbyl groups with pendant carboxyl and pendant polyalkylene oxide groups in defined ratio. The polymers themselves, their preparation, and a process for treating teeth with the compositions are also claimed.

4 Claims, No Drawings

ORAL HYGIENE COMPOSITIONS AND POLYMERS ACTIVE THEREIN

This is a division of application Ser. No. 07/761,463, filed Sep. 18, 1991, now U.S. Pat. No. 5,336,728, which is a Division of application Ser. No. 07/496,150 filed Mar. 19, 1990, now U.S. Pat. No. 5,079,288, which is a continuation of application Ser. No. 07/016,257 filed Feb. 19, 1987, now abandoned, which is a divisional of application Ser. No. 06/793,763 filed Nov. 1, 1985, now abandoned.

This invention relates to oral hygiene compositions, to polymers active therein and to methods of using such compositions to prevent or inhibit attachment of bacteria to teeth.

The prevention of the adherent deposition of dental plaque on mammalian (particularly human) teeth is a highly desired result. Dental plaque results when cariogenic and other types of bacteria aggregate in colonies on the surface of teeth and form a deposit thereon which adheres tenaciously to the surface. It is believed that the formation of plaque on the surface of a tooth is one of the first steps in the development of dental caries and periodontal disease.

Many attempts have been made to prevent the deposition of plaque on tooth surfaces and to effect removal of plaque from such surfaces. For example, fluoride, brushing and dental flossing treatments have been tried. Such treatments are typically directed to counteracting the secondary effects of plaque on the teeth and gums, or to the removal of plaque that is formed on and adhering to the teeth and surrounding tissue. Such treatments are not, however, entirely successful and must be supplemented with periodic treatment by dental professionals.

Recently it has been proposed that the use of oral compositions which contain certain polymers may be useful in preventing deposition of dental plaque. For example, for such use, certain sulphonated vinyl aromatic polymers are suggested in U.S. Pat. No. 4,375,461; the products of the reaction of long chain aliphatic alkylene amine and trimetaphosphoric acid are suggested in U.S. Pat. No. 4,234,568; certain bis-[4-(alkylamino)-1-pyridinium]alkanes and trimetaphosphoric acid are suggested in U.S. Pat. No. 4,234,568; certain bis-[4-(alkylamino)-1-pyridinium]alkanes are suggested in U.S. Pat. No. 4,206,215; certain sulphonated polyamino acids are suggested in U.S. Pat. No. 4,314,991; and copolymers of glutamic acid and tyrosine are suggested in U.S. Pat. No. 4,339,431.

It has also been claimed in U.S. Pat. No. 3,542,917 that the formation of dental calculus, which is a hard calcified deposit that accumulates on or near tooth surfaces, may be inhibited by treatment of the teeth with a composition containing a polyester of a polycarboxylic acid having 3 to 6 carboxyl groups with a polyalkylene ether having 2 to 4 hydroxyl groups and a molecular weight of 400 to 10,000. In our experience, however, compositions falling within the scope of the claims of U.S. Pat. No. 3,542,917 are not very effective in preventing the adherent deposition of cariogenic bacteria, or the plaque resulting therefrom, on tooth surfaces.

We have now found that certain pharmaceutical compositions (as hereinafter defined) containing certain polymers (also as hereinafter defined) are highly effective for preventing or significantly reducing the adherent deposition of cariogenic and other micro-organisms commonly found in an oral environment, and also dental plaque resulting therefrom, on tooth surfaces or simulated tooth surfaces (made of hydroxyapatite as are mammalian tooth surfaces) when the surfaces are treated therewith.

According to the present invention there is provided an oral hygiene composition comprising an effective amount of at least one polymer which polymer comprises one or more repeating units of general structure A

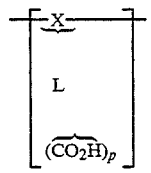

and one or more repeating units of general structure B

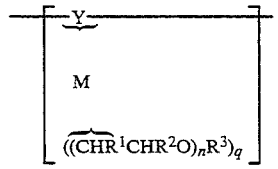

wherein X, which in the repeating units of structure A may be the same or different, and Y, which in the repeating units of structure B may be the same or different, are optionally substituted hydrocarbyl residues providing a backbone for the polymer;

$R^1$, which in the same repeating unit of structure B (when n or q is 2 or more) or in different repeating units of structure B may be the same or different, is hydrogen or methyl;

$R^2$, which in the same repeating unit of structure B (when n or q is 2 or more) or in different repeating units of structure B may be the same or different, is hydrogen or methyl;

except that $R^1$ and $R^2$ in a single unit $(CHR^1CHR^2O)$ cannot both be methyl;

$R^3$, which in the same repeating unit of structure B (when q is 2 or more) or in different repeating units of structure B may be the same or different, is hydrogen, or a lower alkyl group containing up to five carbon atoms, or an acyl group derived from an alkanoic acid having up to five carbon atoms;

n is a number of from 1 to 60;

p is a number of from 1 to 4, and q is a number of from 1 to 4;

and wherein each ($CO_2H$) group is joined via an intermediary or intermediaries L to the hydrocarbyl residue X, and in cases where p is 2 to 4 may be joined by L to the same or different carbon atoms of X;

and wherein L represents one or more intermediaries, and wherein L may be the same or different in the repeat units of structure A and is selected from one or more direct links and one or more groups of atoms each group providing a chain of one or more atoms for linking a ($CO_2H$) group with X, except that more than two ($CO_2H$) groups cannot be directly linked to the same carbon atoms in X;

and wherein each $(CHR^1CHR^2O)_n$ group is joined via an intermediary or intermediaries M to the hydrocarbyl residue Y, and in cases where q is 2 to 4 may be joined by M to the same or different carbon atoms of Y;

and wherein M represents one or more intermediaries, and wherein M may be the same or different in the repeat units of structure B and is selected from one or more direct links and one or more groups of atoms each group providing a chain of one or more atoms for linking a $(CHR^1CHR^2O)_n$ group with Y, except that more than two $(CHR^1CHR^2O)_n$ groups cannot be directly linked to the same carbon atom in Y;

and wherein the ratio of the number of $-CO_2H$ groups to the number of $-CHR^1CHR^2O-$ groups is within the range of from 1:20 to 20:1;

and said composition also comprising a pharmaceutically acceptable vehicle for said polymer.

It is to be understood that the definition of the polymer contained in the composition (as given above) is also intended to embrace a polymer in which at least some of the carboxyl groups in the repeat units of structure A have been converted to the corresponding salt anions $CO_2^-$ (these being considered as $-CO_2H$ groups as far as the ratio of carboxyl to $-CHR^1CHR^2O-$ groups is concerned), the corresponding cations for example being those of (preferably) alkali metals (e.g. $Na^+$, $K^+$), or alkaline earth metals, or ammonium ($NH_4^+$). Such a conversion could be effected as a result of incorporating the polymer into an alkaline pharmaceutically acceptable vehicle, or could be effected by treatment with a suitable alkaline material before incorporation into a pharmaceutical vehicle.

As far as we are aware, polymers falling within the definition as set out above are themselves new and inventive materials.

According there is further provided according to the invention which comprises one or more repeating units of structure A

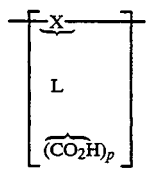

and one or more repeating units of structure B

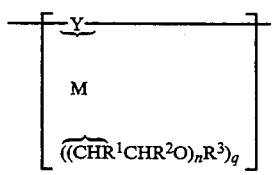

wherein X, Y, $R^1$, $R^2$, $R^3$, n, p, q, L, and M, and the ratio of the number of $-CO_2H$ groups to $-CHR^1CHR^2O-$ groups, are as defined hereinbefore.

In structure A, each carboxyl group is joined to the hydrocarbyl residue X by means of an intermediary or intermediaries (i.e. by a linking entity or entities), this or these being denoted by L, which is selected from one or more direct links (i.e. one or more direct bonds) and one or more groups of atoms each group providing a chain of one or more atoms for linking a carboxyl group(s) with X. In cases where p is 2 to 4, each carboxyl group may be joined by L to the same or, in cases where L represents more than one intermediary, to the same or different carbon atoms in X, although more than 2 carboxyl groups cannot of course be directly linked to the same carbon atom of X (and also assuming that in such cases X has at least 2 carbon atoms, whereas it should be appreciated that it is within the scope of the invention for X to have only 1 carbon atom). It will be noted that in principle L can represent up to 4 separate intermediaries in structure A (in cases where p is 4). L may be the same or different in the repeat units of structure A.

In cases where L represents one or more groups of atoms each group providing a linking chain of atoms, the chain will normally comprise one or more carbon atoms (which could e.g. include carbon atoms in an aryl ring) and/or hetero atoms (particularly N and/or O). Examples of possible linkages provided by L are:

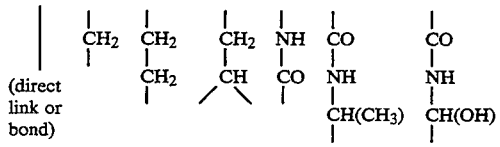

where (apart from the direct link) the top link is to X and the bottom link(s) is to carboxyl. It is preferred in the present invention, however, that L is one or more direct links, so that each carboxyl group is joined directly to a carbon atom of X in the polymer backbone.

It is preferred in structure A that p is 1 or 2 (so that L can then represent one, or at most, two intermediaries).

In structure B, each $(CHR^1CHR^2O)_n$ group is joined to the hydrocarbyl residue Y by means of an intermediary or intermediaries (i.e. by a linking entity or entities), this or these being denoted by M, which is selected from one or more direct links (i.e. one or more direct bonds) and one or more groups of atoms each group providing a chain of one or more atoms for linking a $(CHR^1CHR^2O)_n$ group(s) with Y. In cases where q is 2 to 4, each $(CHR^1CHR^2O)_n$ group may be joined by M to the same or, in cases where M represents more than one intermediary, to the same or different carbon atoms in Y, although more than two $(CHR^1CHR^2O)_n$ groups cannot of course be directly linked to the same carbon atom of Y (and also assuming that in such cases Y has at least 2 carbon atoms, whereas it should be appreciated that it is within the scope of the invention for Y to have only 1 carbon atom). It will be noted that in principle M can represent up to 4 separate intermediaries in structure B (in cases where q is 4). M may be the same or different in the repeat units of structure B.

While M may represent one or more direct links, it is preferred in the present invention that M is one or more groups of atoms each group providing a linking chain of atoms; such a chain will normally comprise one or more carbon atoms (which could e.g. include carbon atoms in an aryl ring) and/or hetero atoms (particularly N and/or O). Particularly preferred examples of linkages provided by M are:

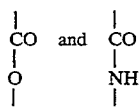

where the top link is to Y and the bottom link is to $(CHR^1CHR^2O)_n$.

It is preferred in structure B that q is 1 or 2 (so that M can then represent one, or at most two intermediaries).

Preferably the structure A represents the repeat unit derived from the polymerisation (usually free-radical initiated) of a polymerisable olefinically unsaturated carboxylic acid. Examples of such acids are acrylic acid, methacrylic acid, maleic (or fumaric) acid, itaconic acid and the acids of formulae

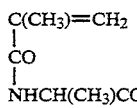 and 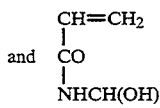

N-methacryloyl alanine    N-acryloyl hydroxy glycine respectively giving rise to the following structures for A:

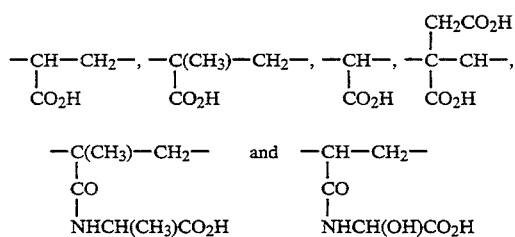

Particularly preferred acids at our present stage of development are methacrylic, acrylic and maleic acid. Normally the repeat units A will all be of the same specific structure, although the scope of the invention is intended to embrace polymers having repeat units A of more than one specific structure (e.g. 2 or 3 different specific structures).

Preferably the structure B represents the repeat unit derived from the polymerisation (usually free-radical initiated) of a polymerisable olefinically unsaturated ester or amide formed from the reaction of an unsaturated carboxylic acid (or an esterifiable or amidifiable derivative thereof such as an acid chloride or anhydride) and a hydroxy compound of formula $HO(CHR^1CHR^2O)_nR^3$ (to form the ester) or an amine of formula $H_2N(CHR^1CHR^2O)_nR^3$ (to form the amide). Preferably the acid used is acrylic or methacrylic acid, particularly the latter, giving rise, respectively, to the following structures for B:

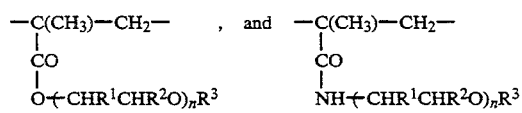

Normally the repeat units B will all be of the same specific structure, although the scope of the invention is intended to embrace polymers having repeat units B of more than one specific structure (e.g. 2 or 3 different specific structures).

The repeating units of structure B may alternatively be formed by the partial esterification or amidification of an already-polymerised olefinically unsaturated carboxylic acid (or an esterifiable or amidifiable derivative thereof such as an acid chloride or anhydride) using, preferably, an alcohol of formula $HO(CHR^1CHR^2O)_nR^3$ or an amine of formula $H_2N(CHR^1CHR^2O)_nR^3$. The remaining (unesterified or unamidified) carboxyl groups with their associated sections of the polymer backbone will of course provide units of structure A (it may of course be necessary to hydrolyse residual acid-derivative groups back to carboxyl when an acid derivative is used).

In one interesting aspect of this alternative method for producing units of structures A and B, an olefinically unsaturated cyclic anhydride may be used to produce both the acid and ester/amide groups of the resulting polymer. For example, maleic anhydride may be polymerised to form a polymer of repeat unit

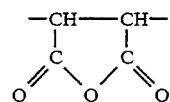

and the resulting repeating units A and B after esterification with $HO(CHR^1CHR^2O)_n R^3$ or amidification with $H_2N(CHR^1CHR^2O)_n R^3$ will be

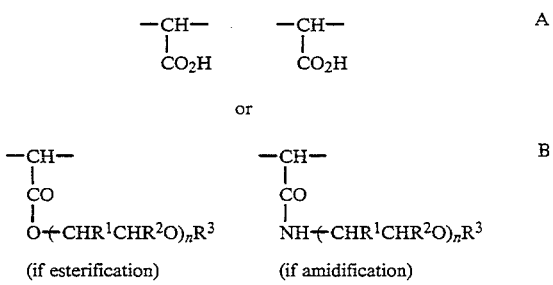

It is thus apparent that there are two preferred processes for preparing polymers according to the invention.

The first process (a) comprises polymerising (usually by free-radical initiation) an olefinically unsaturated carboxylic acid (or an esterifiable or amidifiable derivative thereof) and partially esterifying or amidifying the resulting polyacid (or derivative thereof) with at least one alcohol of formula $HO(CHR^1CHR^2O)_nR^3$ or at least one amine of formula $H_2N(CHR^1CHR^2O)_nR^3$.

The second (and generally more preferred) process (b) comprises copolymerising (usually by free-radical initiation) at least one polymerisable ester or amide, formed from the reaction of a first olefinically unsaturated carboxylic acid (or an esterifiable or amidifiable derivative thereof) and an alcohol of formula $HO(CHR^1CHR^2O)_nR^3$ or an amine of formula $H_2N(CHR^1CHR^2O)_nR^3$, with at least one second olefinically unsaturated carboxylic acid.

Both processes will yield repeat units of structure A and structure B as hereinbefore defined.

In the polymers of the invention, it is preferable that substantially all the $R^1$ and $R^2$ groups are hydrogen so that $(CHR^1CHR^2O)_n$ is $(CH_2CH_2O)_n$. Such groups may be derived from the alcohol $HO(CH_2CH_2O)_nR^3$ or the corresponding amine $H_2N\text{---}(CH_2CH_2O)_nR^3$. Where a proportion of the $R^1$ and $R^2$ groups in the polymer are methyl, all the $R^1$ or $R^2$ groups in one or more of the $(CHR^1CHR^2O)_n$ chains may be methyl or one or more (but not all) of the $R^1$ or $R^2$ groups in one or more of the $(CHR^1CHR^2O)_n$ chains may be methyl. $R^1$ and $R^2$ cannot, however, both be methyl in the same unit $(CHR^1CHR^2O)$ as specified hereinbefore. Such a chain could for example be derived from an amine such as $H_2N\text{---}(CH(CH_3)CH_2O)_2(CH_2CH_2O)_4C_4H_9$ (where $CHR^1CHR^2O$ is $CH(CH_3)CH_2O$ and $CH_2CH_2O$, n is 6, and $C_4H_9$ is normal butyl), or other analogous amines (varying $CHR^1CHR^2O$ and n). It could also be derived from an alcohol, such as $HOCH(CH_3)CH_2OH$.

Preferably $R^3$ is a lower alkyl group containing up to 5 carbon atoms, e.g. n-butyl or (more preferably) methyl. It may, nevertheless, be hydrogen.

Specific examples of polymers that we have prepared and investigated have repeating units structures A and B as follows:

A

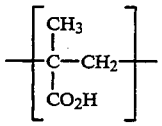

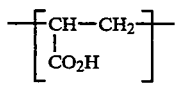

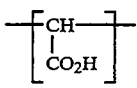

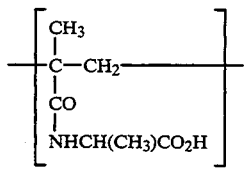

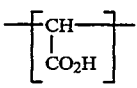

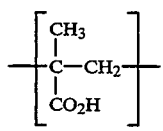

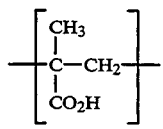

B

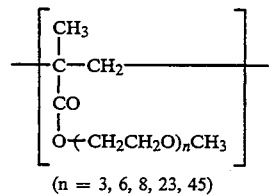

(n = 3, 6, 8, 23, 45)

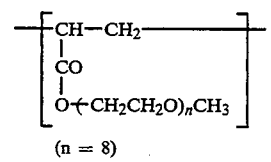

(n = 8)

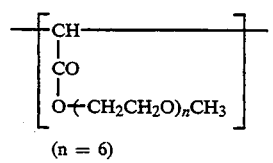

(n = 6)

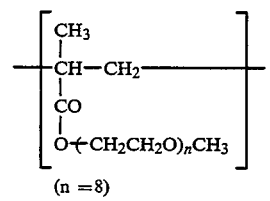

(n =8)

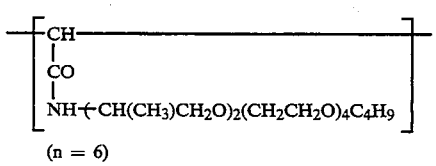

(n = 6)

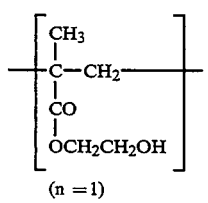

(n =1)

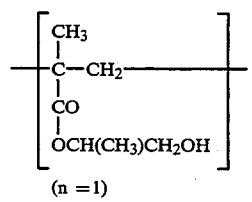

(n =1)

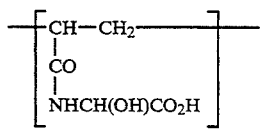

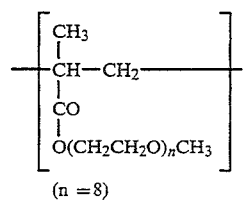

(n = 8)

In the polymers of the invention, n is a number of from 1 to 60 as defined herein. Often, however, n is preferably from 1 to 20. It should be appreciated that most polymers according to the invention (particularly those made with precursors providing the alkyleneoxy grouping that have been obtained commercially) may have a small spread of alkyleneoxy chain length so that n may represent an average value in such cases.

As defined herein, the ratio of $-CO_2H$ groups to $-CHR^1CHR^2O-$ groups is within the range of from 1:20 to 20:1. Preferably the ratio is from 1:5 to 5:1.

Typically the polymers of the invention have weight average molecular weights within the range of from 5000 to 500,000, although we do not exclude the possibility that suitable polymers having molecular weights outside this range may be used in the present invention.

The groups X and Y may be unsubstituted hydrocarbyl radicals or may be substituted with groups such as hydroxy, alkoxy and halogen (chlorine) provided the desired properties of the polymers are not adversely affected. Preferably however, the groups X and Y are unsubstituted, i.e. have only groups linked L and M attached to them.

The polymers of the invention may also contain up to 50% w/w (i.e. 0 to 50% w/w), sometimes up to 10% w/w (i.e. 0 to 10% w/w), of repeating units other than those of structures A and B, which form the backbone thereof, and these may provide one or more in-chain or pendant hetero atoms (per unit). Such other repeating units must not of course adversely affect the properties of the resulting oral hygiene compositions. More usually however, the polymers of the invention have substantially all their repeating units with structures A and B.

The oral hygiene compositions of the invention generally have said at least one polymer present therein at a concentration of about 0.05 to 30 weight % of the composition, the preferred concentration range being from about 0.1 to 5 weight % (and more preferably 0.2 to 2 weight %).

While the oral hygiene compositions of the invention will usually have only one polymer according to the invention (as defined hereinbefore) therein, it is quite feasible to use two or more such polymers in the compositions.

Suitable conventional pharmaceutically acceptable vehicles that can be employed in the oral hygiene compositions of the present invention include water, ethanol (wherein water, or a water/ethanol mixture will often be a major component of the vehicle); such humectants as polypropylene glycol, glycerol and sorbitol; such geling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilisers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; surfactants such as sodium lauryl sulfate, sodium cocomonoglyceride sulfonate, sodium lauryl sarcosinate and polyoxyethylene isohexadecyl ether (Arlasolve 200) and approved colours and flavours.

The oral hygiene compositions of the invention may be in the form of any conventional pharmaceutically acceptable oral hygiene formulation that contains (and is compatible with) an effective amount of a polymer as defined herein. Such formulations include, for example, mouthwashes, rinses, irrigating solutions, abrasive and nonabrasive gel dentifrices, denture cleansers, coated dental floss, coated or impregnated toothbrush bristle (natural or synthetic), and interdental stimulator coatings, chewing gums, lozenges, breath fresheners, foams and sprays.

The present invention is now illustrated by the following examples. The prefix C for a number denotes a comparative example.

EXAMPLES 1 TO 17, AND C18 TO C23

Examples 1 to 17 illustrate polymers (and their preparation) according to the present invention of which polymers oral hygiene compositions according to the invention may be comprised. It was found that comonomers providing units A and B reacted so as to give polymers in which the mole ratio of A to B units therein was close to the mole ratio used for the starting monomers (indicating approximately equal reactivities), so that the latter ratio could be used for calculating the former, which was also checked in most cases using ordinary analytical techniques (chemical analysis, NMR, and acid-base titrations).

A typical polymer preparation, specifically applicable to the polymers of Examples 1 to 6, 9, 10, and 12 is now described. (Dry chemicals and solvents were used.)

Methacryloyl chloride (0.11 moles) was added slowly with stirring to a slight molar excess of a 30% solution of 2,6-lutidine in toluene. Fuming occurred and a white precipitate formed. The mixture was cooled in an ice-bath and methoxy-ended polyethylene glycol (0.10 moles) was added dropwise ever 3 hours with stirring under nitrogen. A copious white precipitate formed and stirring was continued for a further 2 hours. The reaction mixture was allowed to warm to room temperature. The precipitate was filtered off and washed with small volumes of toluene. The combined filtrates were evaporated to dryness (over 90% yield) on a rotary evaporator at 45° C. The structure of the product was confirmed, by IR, NMR and vinyl bond titration, as substantially α-methoxy-δ-methacryloyloxy-polyethylene glycol.

The monomers methacrylic acid and α-methoxy-δ-methacryloyloxy-polyethylene glycol, in selected molar ratios (total 25 grams), and solvent (usually ethanol or ethanol/water mixture) (300 ml) were charged to a reaction vessel at 70° C. Initiator ($1.8 \times 10^{-3}$ moles) in solvent (20 mls) was added and the reaction mixture was stirred (200 rpm) at 70° C. for 24 hours. Further (initiator ($7 \times 10^{-4}$ moles) in solvent (20 ml) was added and the reaction was continued for a further 24 hours. The reaction mixture was evaporated on a rotary evaporator under reduced pressure to leave a copolymer (usually about 95% yield). The compositions of the copolymers are given in Table 1, which also gives the values for n and the ratio of ($CO_2H$) to ($CHR^1CHR^2O$) groups.

Substantially the same sort of technique was employed for the preparation of the polymers of Examples 7, 8, 11, 13, 14, 16 and 17 except that:
- for the preparation of the polymer of Example 7, acrylic acid was used in place of methacrylic acid for the polymerisation
- for the preparation of the polymer of Example 8, N-methacryloyl alanine, i.e. $CH_2=CH(CH_3)CONH(CH_3)CO_2H$, prepared by reacting the Na salt of alanine with methacryloyl chloride, was used in place of methacrylic acid for the polymerisation
- for the preparation of the polymer of Example 14, N-acryloyl hydroxy glycine, i.e. $CH_2=CHCONHCH(OH)CO_2H$, was used in place of methacrylic acid for the polymerisation
- for the preparation of the polymers of Examples 13 and 17, there was used, respectively, hydroxyethyl methacrylate and hydroxypropyl methacrylate in place of α-methoxy-δ-methacryloyl-polyethylene glycol.
- for the preparation of the polymer of Example 11, the N-methacryloyl derivate of $C_4H_9(OCH_2CH_2)$-$4(OCH_2CH(CH_3))_2NH_2$, i.e. $CH_2=CH(CH_3)CONH(CH(CH_3)CH_2O)_2$ $(CH_2CH_2O)_4C_4H_9$ was used in place of α-methoxy-δ-methacryoyloxy-polyethylene. This monomer was made by reacting the amino compound with methacryloyl chloride in toluene as solvent and in the presence of 2,6-dimethyl pyridine as acid acceptor
- for the preparation of the polymer of Example 16, the polymerisation was photo initiated at room temperature using benzoin methyl ether.

The compositions of these polymers are also given in Table 1.

The polymer of Example 15 was prepared by the alternative technique of partially esterifying or amidifying an already-polymerised carboxy acid or derivative thereof. A maleic anhydride/methyl vinyl ether copolymer (1/1 molar) of medium molecular weight (Aldrich) was reacted at an elevated temperature with the calculated amount of $C_4H_9(OCH_2CH_2)$-$4(OCH_2CH(CH_3))_2NH_2$ (available commercially), under anhydrous conditions to provide a partially amidified product (each anhydride group reacting with the amine forming adjacent carboxyl and amido groups). This product was then heated with water (excess) to hydrolyse the residual unreacted anhydride groups to form adjacent carboxyl groups. This yielded, respectively, the repeating units

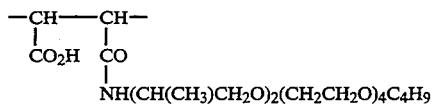

and

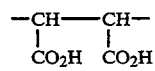

so that the repeat units of structures A and B were respectively

and

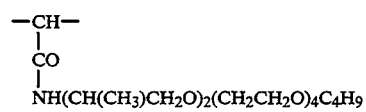

The composition of this polymer is also given in Table 1.

The polymers of C18 to C21 were prepared for comparative purposes, using substantially the same technique as used for Examples 1 to 6, etc, except that:
- for the preparation of the polymers of Examples C18, C19 and C20 the monomers for the polymerisations also included methyl methacrylate (MMA) which therefore became incorporated into the polymer backbone. The molar ratio of MA:MMA used in these three examples was 10:1
- for the preparation of the polymer of Example C21, the MA monomer was replaced entirely by MMA, so that the polymer contained no acidic A units The compositional details of these comparative polymers is also given in Table 1.

The weight average molecular weights of most of the polymers were determined (using gel permeation chromatography with polystyrene or polyethylene oxide standards, and dimethyl formamide or tetrahydrofuran as solvent) and were mostly within the range 5000 and 500,000.

The product of Example 8 of U.S. Pat. No. 3,542,917 was also prepared for comparative purposes, being denoted by Example C22. Example C23 denotes an analogous product to that of Example 8 of U.S. Pat. No. 3,542,917 but using polyethylene glycol in place of polypropylene glycol.

TABLE 1

| Ex. No. | Repeating Unit | | Other Units | Value of n | Molar Ratio of A:B | Ratio of ($CO_2H$):($CHR^1CHR^2O$) groups (approx.) |
|---|---|---|---|---|---|---|
| | Type A | Type B | | | | |
| 1 | MA | PEG350MAt | — | 8 | 3:1 | 1:2.7 |
| 2 | MA | PEG2000MAt | — | 45 | 3:1 | 1:15 |
| 3 | MA | PEG2000MAt | — | 45 | 10:1 | 1.4.5 |

TABLE 1-continued

| Ex. No. | Repeating Unit Type A | Repeating Unit Type B | Other Units | Value of n | Molar Ratio of A:B | Ratio of ($CO_2H$):($CHR^1CHR^2O$) groups (approx.) |
|---|---|---|---|---|---|---|
| 4 | MA | PEG150MAt | — | 3 | 3:1 | 1:1 |
| 5 | MA | PEG350MAt | — | 8 | 6:1 | 1:1.3 |
| 6 | MA | PEG1000MAt | — | 23 | 3:1 | 1:7.7 |
| 7 | AA | PEG350MAt | — | 8 | 3:1 | 1:2.7 |
| 8 | MAtAl | PEG350MAt | — | 8 | 3:1 | 1:2.7 |
| 9 | MA | PEG350MAt | — | 8 | 10:1 | 1.25:1 |
| 10 | MA | PEG350MAt | — | 8 | 3.5:1 | 1:2.3 |
| 11 | MA | JMAt | — | 6 | 6:1 | 1.1:1 |
| 12 | MA | PEG1000MAt | — | 23 | 25:1 | 1:1 |
| 13 | MA | HEMAt | — | 1 | 1:1 | 1:1 |
| 14 | NG | PEG350MAt | — | 8 | 6:1 | 1:1.3 |
| 15 | MaI | MalJ | MEV | 6 | 7:1 | 1.17:1 |
| 16 | MA | PEG350MAt | — | 8 | 6:1 | 1:1.3 |
| 17 | MA | HPMAt | — | 1 | 1:1 | 1:1 |
| C18 | MA | PEG550MAt | MMA | 12 | 1:2.75 | 1:33 |
| C19 | MA | PEG2000MAt | MMA | 45 | 1:2 | 1:90 |
| C20 | MA | PEG350MAt | MMA | 8 | 1:2.75 | 1:22 |
| C21 | — | PEG350MAt | MMA | 8 | no A | no A |
| C22 | As for Ex 8 of U.S. 3542917 | | | | | |
| C23 | As for Ex 8 of U.S. 3542917 but using PEG instead of PPG | | | | | |

Abbreviations in Table 1

MA: units derived from methacrylic acid.
PEG350MAt: units derived from polyethylene glycol (PEG) capped with a methoxy and a methacryloyl group, i.e. from $CH_2=C(CH_2)COO(CH_2CH_2O)_nCH_3$ where the molecular wt of the polyethylene glycol (PEG) portion thereof is 350.
PEG2000MAt: as PEG350MAt but with PEG portion molecular wt of 2000.
PEG150MAt: as PEG350MAt but with PEG portion molecular wt of 150.
PEG1000MAt: as PEG350MAt but with PEG portion molecular wt of 1000.
PEG550MAt: as PEG350MAt but with PEG portion molecular wt of 550.
AA: units derived from acrylic acid.
MAtAl: units derived from N-methacryloyl alanine, i.e. from $CH_2=CH(CH_3)CONHCH(CH_3)CO_2H$
JMAt: units derived from amide formed between methacrylic acid and the amine of formula $NH_2(CH(CH_3)CH_2O)_2(CH_2CH_2O)_4C_4H_9$, i.e. from $CH_2=CH(CH_3)CO-NH(CH(CH_3)CH_2O)_2(CH_2CH_2O)_4C_4H_9$ where $C_4H_9$ is normal butyl.

MaI:
units of formula $\overset{|}{\underset{|}{CH}}-CO_2H$

MalJ: units of formula $\overset{|}{\underset{|}{CH}}CONH(CH(CH_3)CH_2O)_2(CH_2CH_2O)_4C_4H_9$ MEV: units derived from methyl vinyl ether.
MMA: units derived from methyl methacrylate.
HEMAt: units derived from hydroxyethyl methacrylate.
HPMAt: units derived from hydroxypropyl methacrylate.
NG: units derived from N-acryloyl hydroxy glycine.
PPG: polypropylene glycol.

EXAMPLES 24 TO 40 AND C41 TO C46

These examples illustrate the extent of the reduction in bacterial adhesion obtained with use of the polymers hereinbefore defined.

Polished hydroxyapatite discs (25 mm diameter) were used as a model tooth surface. *S. mutans* NCTC 10449 was used as the standard organism.

The discs were used clean or were pellicle-coated by incubating in freshly collected whole saliva (from a single donor) for 1 hour at 37° C., followed by brushing with water 5 times.

The aforementioned discs were held in a 1% w/v aqueous (or alcoholic) solution of the polymers in a petri-dish for 5 minutes at ambient temperature and were then washed by shaking 5 times in a container of flowing water ("treated discs").

S. mutans NCTC 10449 were grown at 37° C. in a Brain/Heart Infusion growth medium. A portion (20 mls) of the culture at a concentration of $10^9$ cells/ml was centrifuged at 4,000 rpm for 10 minutes and the cells were resuspended in modified Ringer's salts solution (0.54 grams per liter NaCl; 0.02 grams per liter KCl; 0.03 grams per liter $CaCl_2$; and 0.75 grams per liter sodium mercaptoacetate), recentrifuged, resuspended and diluted 10× in Ringer's salts solution.

The treated discs were immersed in the aforementioned suspension for 2 hours. The treated discs were then washed by shaking 5 times in a container of flowing water and bacteria adhering thereto were stained using Loeffler's Methylene Blue (30 ml of 95% ethanol, 0.3 gram methylene blue and 100 ml of water). Microscopic examination was used to estimate the reduction in bacterial adhesion of the clean discs and pellicle-coated discs versus untreated control discs. The results for the clean discs are given in Table 2.

TABLE 2

| Example No. | Polymer from Ex. No. | % Reduction[a] compared with untreated control discs |
|---|---|---|
| 24 | 1 | 96 |
| 25 | 2 | 74 |
| 26 | 3 | 92 |
| 27 | 4 | 97 |
| 28 | 5 | 98 |
| 29 | 6 | 93 |
| 30 | 7 | 91 |
| 31 | 8 | 90 |
| 32 | 9 | 95 |
| 33 | 10 | 95 |
| 34 | 11 | 97 |
| 35 | 12 | 96 |
| 36 | 13 | 98 |
| 37 | 14 | 99 |
| 38 | 15 | 99 |
| 39 | 16 | 99 |
| 40 | 17 | 99 |
| C41 | C18 | 25 |
| C42 | C19 | +17 |
| C43 | C20 | +18 |
| C44 | C21 | 0 |
| C45 | C22 | 15 |
| C46 | C23 | +41 |

[a]average of several discs
+ denotes an increase in adhesion rather than a reduction In the case of pellicle-coated discs, the results of extensive testing using selected polymers, viz those of Examples 1, 5, and 6, were 90%, 97% and 87% reduction respectively.

EXAMPLES 47 AND 48

Examples 24 and 28 were repeated using extracted human teeth which had been brushed. Similar results were obtained.

EXAMPLES 49 TO 54

The polymer of Example 5 was tested for its effectiveness in preventing the adherent deposition of a range of oral bacteria other than S. mutans NCTC 10449, the evaluation procedure being otherwise the same as in Examples 24 to 40, C41 to C46 (clean discs only). The results are given in Table 3.

TABLE 3

| Example No. | Bacteria | % Reduction compared with untreated control discs |
|---|---|---|
| 49 | S. sanguis 11085 | 96 |
| 50 | S. salivarious 11389 | 99 |
| 51 | Streptococcus Group H1 | 99 |
| 52 | Streptococcus Group H2 | 99 |
| 53 | Saliva Isolate A | 98 |
| 54 | Saliva Isolate B | 99 |

EXAMPLES 55 TO 68, AND C69

A number of polymers according to the invention, identified as being extremely promising by the petri-dish experiments described in the preceding examples, were subjected to a more severe challenge using flowing conditions in order to more closely simulate the environment inside a mammalian (human) mouth. A "Drip-Machine" was developed for this purpose, and consisted of a glass reservoir containing approximately 400 ml of a stirred solution of S. mutans (prepared as for the petri-dish experiments). An 8 channel peristaltic pump was used continuously to drip (using syringe needles) 8 flows of the bacterial suspension over 8 samples (clean hydroxyapatite discs treated with 1% aqueous (or alcoholic) solution of polymer, or untreated, as before) suspended on a mesh above the reservoir, the bacterial suspension thus being recycled. The tests were carried out in an incubating oven at 37° C. and experiments were routinely run overnight (about 17–19 hours). After the adhesion stage, the substrates were washed, stained and examined, as in the petri-dish experiments described above. A composition containing the polymer of Example C22 was also tested for comparison purposes. The results are shown in Table 4.

TABLE 4

| Example No. | Polymer from Ex. No. | % Reduction compared with untreated control discs |
|---|---|---|
| 55 | 1 | 64 |
| 56 | 3 | 68 |
| 57 | 4 | 88 |
| 58 | 5 | 94 |
| 59 | 6 | 63 |
| 60 | 7 | 91 |
| 61 | 8 | 60 |
| 62 | 11 | 90 |
| 63 | 12 | 98 |
| 64 | 13 | 36 |
| 65 | 14 | 99 |
| 66 | 15 | 95 |
| 67 | 16 | 99 |
| 68 | 17 | 99 |
| C69 | C22 | +25 |

+ denotes an increase in adhesion rather than a reduction.

It can be seen that all the polymer compositions according to the invention used in Examples 55 to 68 gave a positive degree of utility for preventing adherent bacterial deposition under the more severe testing conditions employed in the "Drip-Machine", and those containing the polymers of Example 5, 7, 11, 12, 14, 15, 16, and 17 were particularly noteworthy by giving % reductions of 90 or above even under these more severe conditions.

We claim:

1. An oral hygiene composition consisting essentially of an aqueous solution of an effective amount of at least one polymer and a pharmaceutically acceptable vehicle, which polymer consists of one or more repeating units of general structure A

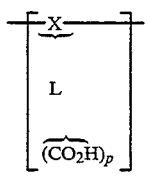

and one or more repeating units of general structure B

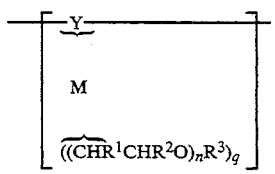

wherein X is $CH_2C(CH_3)$; Y is $-CH_2C(CH_3)-$; $R^1$ is hydrogen; $R^2$ is hydrogen; $R^3$ is methyl; n is about 8; p is equal to 1, and q is equal to 1; and wherein each ($CO_2H$) group is joined via a direct link L to X; and wherein each ($CHR^1CHR^2O)_n$ group is joined via an intermediary M to the hydrocarbyl residue Y such that M is COO; and wherein the ratio of repeating units A to B is about 6:1.

2. A composition according to claim 1 wherein said polymer is present therein at a concentration of 0.05 to 30 weight % of the composition.

3. A composition according to claim 1 in the form of a mouthwash, rinse, irrigating solution, abrasive or non-abrasive gel dentifrice, denture cleaner, coated dental floss, toothbrush bristle coating or impregnant, interdental stimulator coating, chewing gum, lozenge, breath freshener, foam or spray.

4. A composition according to claim 2 in the form of a mouthwash, rinse, irrigating solution, abrasive or non-abrasive gel dentifrice, denture cleaner, coated dental floss, toothbrush bristle coating or impregnant, interdental stimulator coating, chewing gum, lozenge, breath freshener, foam or spray.

* * * * *